US00PP16977P2

(12) United States Plant Patent
Wassum

(10) Patent No.: US PP16,977 P2
(45) Date of Patent: Aug. 8, 2006

(54) ALMOND TREE NAMED 'WASSUM'

(50) Latin Name: *Prunus dulcis*
Varietal Denomination: Wassum

(76) Inventor: Mike Wassum, 1779 Santa Fe Ave., Hughson, CA (US) 95326

( * ) Notice: Subject to any disclaimer, the term of this patent is extended or adjusted under 35 U.S.C. 154(b) by 74 days.

(21) Appl. No.: 10/746,585

(22) Filed: Dec. 23, 2003

(51) Int. Cl.
*A01H 5/00* (2006.01)

(52) U.S. Cl. ..... Plt./155
(58) Field of Classification Search ..... Plt./155
See application file for complete search history.

*Primary Examiner*—Kent Bell
*Assistant Examiner*—June Hwu
(74) *Attorney, Agent, or Firm*—Bernhard Kreten; Audrey A. Millemann; Weintraub Genshlea Chediak

(57) ABSTRACT

A new and distinct variety of almond tree that is somewhat similar to the 'Carmel' and 'Nonpariel' varieties, but is distinguished therefrom in being slightly darker in color than the 'Carmel' and in having a larger kernel than the 'Nonpariel'. In addition, the fruit is produced several days after both 'Carmel' and 'Nonpariel' varieties. The fruit is of medium size and has a soft shell. This new invention has a good flavor and is free from an unusual number of doubles (kernels in the shell).

1 Drawing Sheet

BACKGROUND OF THE NEW VARIETY

The present invention relates to a new and distinct variety of almond tree, *Prunus dulcis,* which will hereinafter be denominated varietally as 'Wassum', and relates particularly to an almond tree which produces nuts (fruit) for commercial harvesting, hulling, shelling and shipping during the 4th week of August, several days after 'Nonpariel' and 'Carmel', in the Hughson area of the San Joaquin Valley of Central California, and which is further distinguished by producing medium soft-shelled almonds having a good flavor, slightly darker in color than 'Carmel' and with slightly larger kernel than 'Nonpariel', as well as being a heavier producer than either of the aforementioned varieties.

There are a number of criteria of which commercial varieties of tree fruits and nuts must be of superior nature to be a commercial 'success'; these criteria include, but are not limited to, maturity date, flavor, storage ability and shipping ability. With tree fruits as well as nuts such as almonds, maturity date earlier in the harvest season, the quality of the meat of the kernel, freedom from an unusual number of doubles, and a reasonably soft shell makes this almond commercially attractive with a substantial likelihood of commercial success.

Almond varieties differ as to the type of shell (soft or hard); the latter characteristic makes kernel removal difficult, making marketing more difficult. High quality of the kernel as well as comparative ease of shelling with low percentage of double provides excellent appeal to the purchaser.

ORIGIN AND ASEXUAL REPRODUCTION OF THE NEW VARIETY

The present invention or almond tree was discovered by the inventor as a volunteer seeding in a commercial planting of 'Nonpariel' (unpatented) and 'Carmel' varieties of almond trees in late 1980 on the east side of Santa Fe Avenue on the outskirts of the town of Hughson, Calif. After several years of observation 21 trees were budded onto Nemaguard Rootstock (1990/91). Nineteen trees survived and produced nuts that are identical in all respects to the original tree. An additional 1½ acres have been planted, grafted on Nemaguard Rootstock and are now in their 3rd leaf (2002) (3 years old), 4th leaf in 2003 (4 years old).

SUMMARY OF THE NEW VARIETY

The 'Wassum' almond is characterized by producing a medium soft-shelled almond which has good flavor and larger kernels than 'Nonpariel' almond and is mature for commercial harvesting and shipment during the 4th week of August in the Hughson area of the San Joaquin Valley of Central California. The new variety is most similar to 'Carmel' variety, but is slightly darker in color and produces nuts several days after 'Carmel' and 'Nonpariel' almonds. The kernel (nut) has a very good flavor and should be very acceptable to the consumer.

BRIEF DESCRIPTION OF THE DRAWING

The accompanying drawing, a colored photograph, shows the following: At the bottom of the photograph there are several almonds with husks still attached to twigs, several husks splitting displaying the almond shells, several almonds out of the hull displaying the shape of the shell, several almond kernels displaying their size and shape and, finally, the terminal foliage displaying size and shape of the leaves.

DETAILED DESCRIPTION

Referring more specifically to the pomological description of this new and distinct variety of almond tree, the following has been observed under the ecological conditions prevailing in the orchard of origin which is located near Hughson, Calif. in the San Joaquin Valley of Central California. All major color code designations are by reference to the Dictionary by Color of Maerz and Paul, First Edition, 1930. Common color names are occasionally employed.

Tree

Size — Tree is similar in size to 'Nonpariel' and 'Carmel' almond — ten to twelve feet high and 6–9 feet wide. Upright but not spread as much as 'Nonpariel' or 'Carmel' varieties of almond trees.
Vigor — good.
Density — heavy foliage with many small branches.
Regulatory of bearing: Regular.

Trunk

Size — circumference 32 inches, 12 inches aboveground. Surface Texture — rough.
Color code — P1.7 H7 Cedar+.
Lenticles — Number — approximately 15–20 over 6 inches of the trunk.
*Size.*—Medium — 5–9 mm (0.21–0.35 inches) Oval form.
*Color.*—P1. 7 J7 Roan.

Branches

Size — moderate — 6–8 inches in circumference, 40" aboveground, 58° angle of branches at crotch of tree.
Surface texture —
*Mature.*—Slightly rough.
*Immature.*—Smooth.
Color code — Mature (1 yr. or older), P1.46 D6, Plumbago slate+Immature — P1.18 J7 — Spring green.
Lenticles
*Size.*—Numbers — small.
*Color.*—Slightly darker than P1.46 D6 Plumbago slate.

Flowers

Bloom — 75–80% on Mar. 19, 2003.
Clusters — 4–5 buds in cluster.
Buds — diameter 6–8 mm (0.24–0.31 inch).
*Length.*—9–11 mm (0.35–0.48 inch).
*Color of bud tips.*—P1.2 C3 Light pink.
Calyx — 5 sepals. Color base and Margins, P1.22 C7 Cactus.
*Apex.*—P1.55 L12 vineyard oporto+.
*Length.*—6–7 mm (0.24–0.28 inch).
*Diameter.*—3–5 mm (0.12–0.20 inch).

Blossom

Petals — 5.
Diameter of blossoms — 35–48 mm (1.38–1.89 inch).
*Petals.*—length — 15–20 mm (0.59–0.79 inch).
*Width.*—13–15 mm (0.51–0.59 inch).
*Margins.*—undulated and notched.
Color of the bloom — some of the flowers have light pink color, P1.1 B1.
Pistil — 1 — 10–13 mm (0.39–0.51 inch), long color P1.19 K3 Chrysolite gr.
Stamens — 23–34 — length — 5–10 mm (0.12–0.39 inch). Filament white near top — base P1.2 J3 Rose Nilson.
Anthers — size — small, less than 1 mm.
*Color.*—P1.9 L4 Sunflower Dandelion.

Leaves

Foliage — prolific.
*Size.*—Length — 80–145 mm (3.15–5.71 inch).
*Width.*—38–34 mm (1.10–1.34 inch).
*Shape.*—Lanceolate.
*Thickness.*—Normal for almond.
*Color code.*—Upwardly disposed surface — P1.22 L7 Art Green. Downwardly disposed surface — P1.23 S8 Mt. Vernon gr.
*Marginal form.*—Crenate.
*Leaf vein.*—Color Code — P1.18 H5 Near sky green. Thickness — 1½ mm (0.6 inch).
*Leaf glands.*—2–4 reniform. Size — 2–3 mm (.079–0.12 inch).
*Petiole.*—Length — 30–35 mm (1.18–1.38 inch). Thickness — 1 mm (0.04 inch). Color Code — P1.18 H5 Near sky green.
*Petiole sinus.*—Based is tapered and no sinus.
*Stipules.*—2, prominent, P1.8 L4 Andorra.
Crop — productivity — excellent, over 3000 lbs/acre.
Harvest period — 4th week of August.
Distribution of nuts on tree — Uniform throughout the tree.
Tenacity — 7,000.
Hull:
*Texture.*—Grooved.
*Pits.*—None.
*Form.*—Ovate.
*Thickness.*—14–17 mm (0.55–0.67 inch).
*Color.*—P1.37 A3 Chinchilla.
Suture — None.
Dehiscence — Good.
Hull thickness — 4 mm (0.157 inch).

Nut (Shell)

Size—
*Length.*—35–40 mm (1.38–1.57 inch).
*Width.*—14–15 mm (0.55–0.59 inch).
*Thickness.*—15 mm (0.59 inch).
Form — ovate.
Thickness — 15 mm (0.59 inch).
Shell — outer — flake.
*Inner.*—Brittle.
Peduncle — 5–7 mm in length (0.20–0.28 inch) 4 mm (0.16 inch) diameter.
*Color.*P1.37 A2 New silver dawn gy.
Color — P1.12 L4 Sulphiney to P1.12 L6 Tennis.
Pits — small.
Base — rounded on keel side, slightly sloped toward stem end of shell.
Stem scar — prominent.
Apex — pointed.
Wing —
Inner surface — smooth.
Ventral streak
*Color.*—Same as shell, P1.12 L4 to P1.12 L6 (Sulphiney to Tennis).
*Percent kernel to nut.*—51–52%.

Kernel

Size — About 15% larger than 'Nonpariel', about same size as 'Carmel' variety (App. 400 kernel/lb.).
*Length.*—26–28 mm (1.02–1.10 inch).
*Width.*—12–14 mm (0.47–0.55 inch).
*Thickness.*—8–9 mm (0.31–0.35 inch).
Form — ovate.
Thickness — 8–9 mm (0.31–0.35 inch).
Base — slightly rounded.
Stem scar — not apparent.
Apex — pointed.
Surface texture — Ribbed, similar to 'Carmel'.

Pellicle —
*Thickness.*—Very thin.
Pubescence — none apparent.
Color — P1.6 F11 Saona — slightly darker than 'Carmel' kernel.
Number of doubles produced — approximately 2–2½%.
Flavor — very good.
Quality — very good.
Use — fresh market etal.
Keeping and shipping quality — excellent.
Resistance to disease — appears to be somewhat resistant to "Crazy Top", a virus disease that causes erratic top growth with bud failure.
Harvest — fourth week of August.
Has the new variety been sold? — No.
Has any reproducible parts on the plant been given away? — No.
Name of the new variety — 'Wassum'.
Pollenizer — 'Nonparel' or 'Carmel' varieties.

LAST STATEMENT

Although the new variety of almond tree possesses the described characteristics noted above as a result of the growing conditions prevailing in the Hughson area of the San Joaquin Valley of Central California, it is to be understood that variations of the usual magnitude and characteristics incident to changes in growing conditions, fertilization, pruning and pest control are to be expected.

I claim:

1. A new and distinct variety of almond tree substantially as illustrated and described.

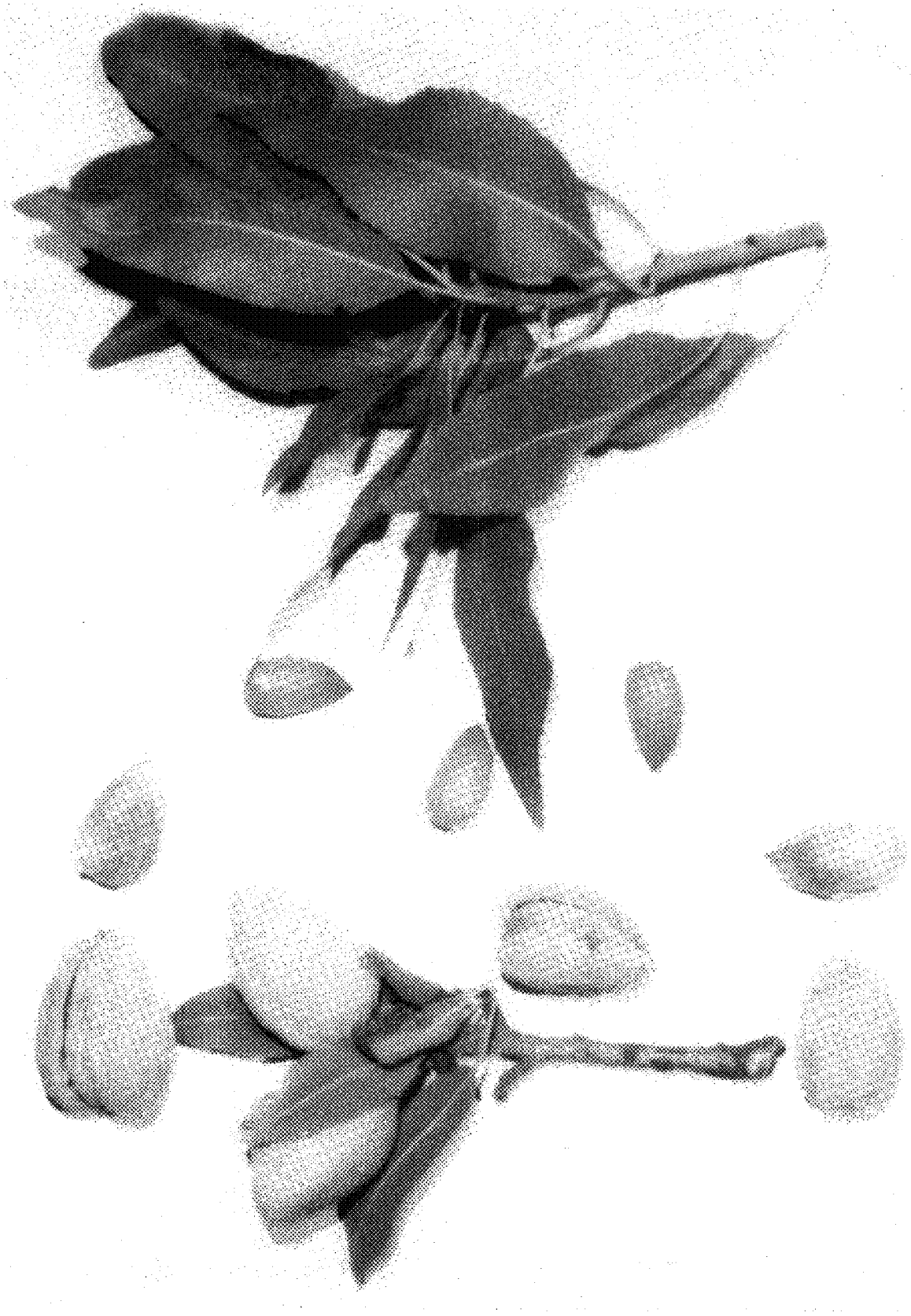

* * * * *